United States Patent [19]

Mays

[11] Patent Number: 4,884,970

[45] Date of Patent: Dec. 5, 1989

[54] ATTACHMENT FOR REMOVABLY SUPPORTING A DENTURE IN THE MOUTH OF THE USER

[76] Inventor: Ralph C. Mays, 6740 S. 69th East Ave., Tulsa, Okla. 74133

[21] Appl. No.: 264,858

[22] Filed: Oct. 31, 1988

Related U.S. Application Data

[63] Continuation-in-part of Ser. No. 221,212, Jul. 19, 1988, which is a continuation-in-part of Ser. No. 90,456, Aug. 28, 1987, Pat. No. 4,784,608.

[51] Int. Cl.$^4$ ............................................. A61C 13/22
[52] U.S. Cl. .................................... 433/172; 433/173
[58] Field of Search ................................ 433/172, 173

[56] References Cited

U.S. PATENT DOCUMENTS 2,644,231 7/1953 Brennan ............................ 433/173
4,085,506 4/1978 Lew .................................... 433/172

Primary Examiner—Robert Peshock
Attorney, Agent, or Firm—Head & Johnson

[57] ABSTRACT

An attachment for pivotally supporting a denture in the mouth of the user in which the user has at least two spaced apart dental posts implanted therein, such posts being in the front of and one to either side of the front center of the mouth of the user, the attachment including an anchor member semi-permanently attached to the anchor posts and having a bar portion extending between the spaced apart dental posts. A denture member which conforms generally to the contour of the anchor member is engagable in proximity with the anchor member bar portion. The denture member is cast within a denture having simulated gum portions and teeth portions. The denture member has an arm for removably and pivotally interlocking the denture member with the anchor member bar portion when a denture having the denture member formed therein is in a usable position within the mouth of the user. Pivotation limiting trunnions are formed as a part of the anchor member. The trunnions serve to limit the angle of pivotation of the denture member relative to the anchor member.

6 Claims, 3 Drawing Sheets

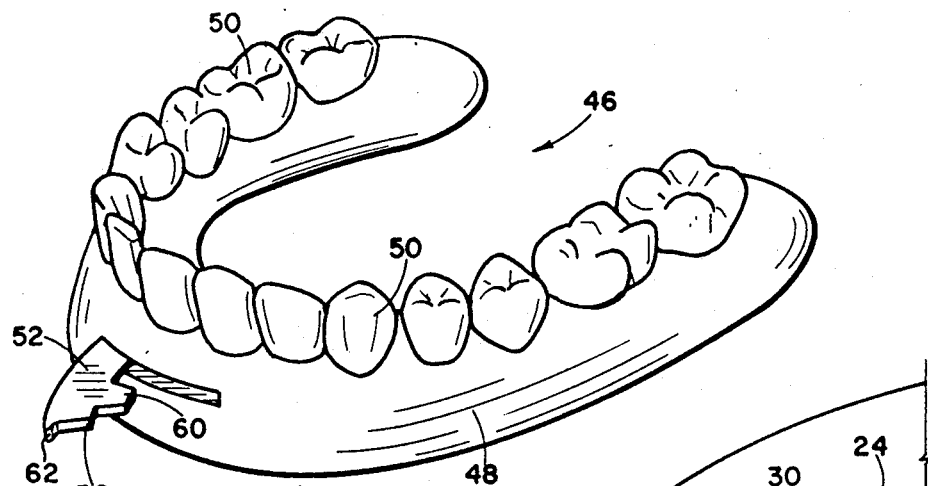
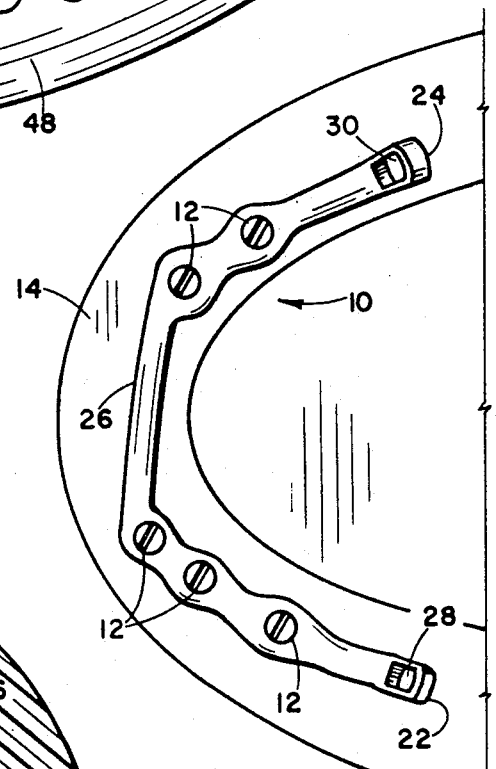
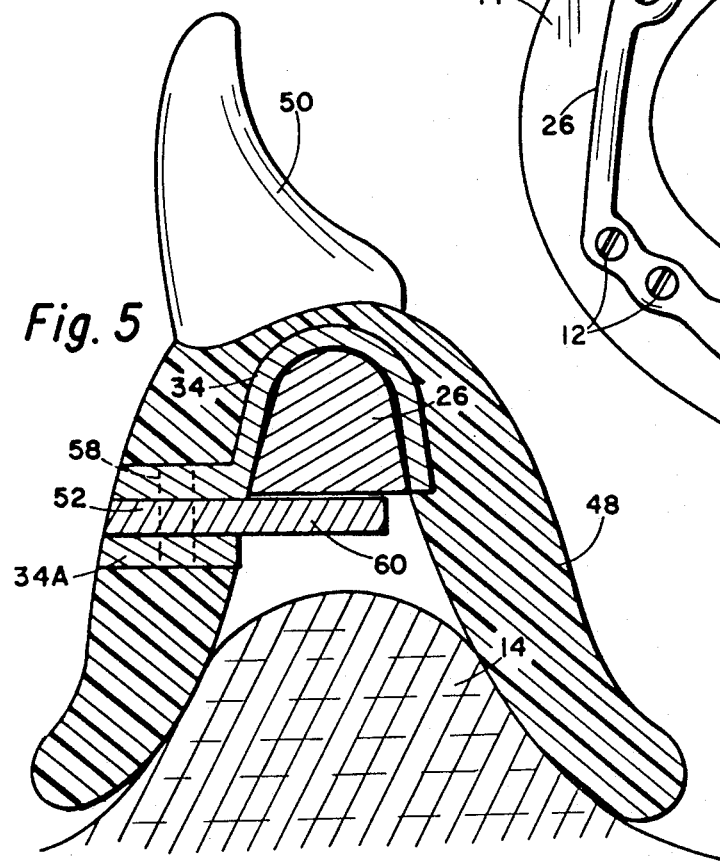
Fig. 3
Fig. 5
Fig. 1

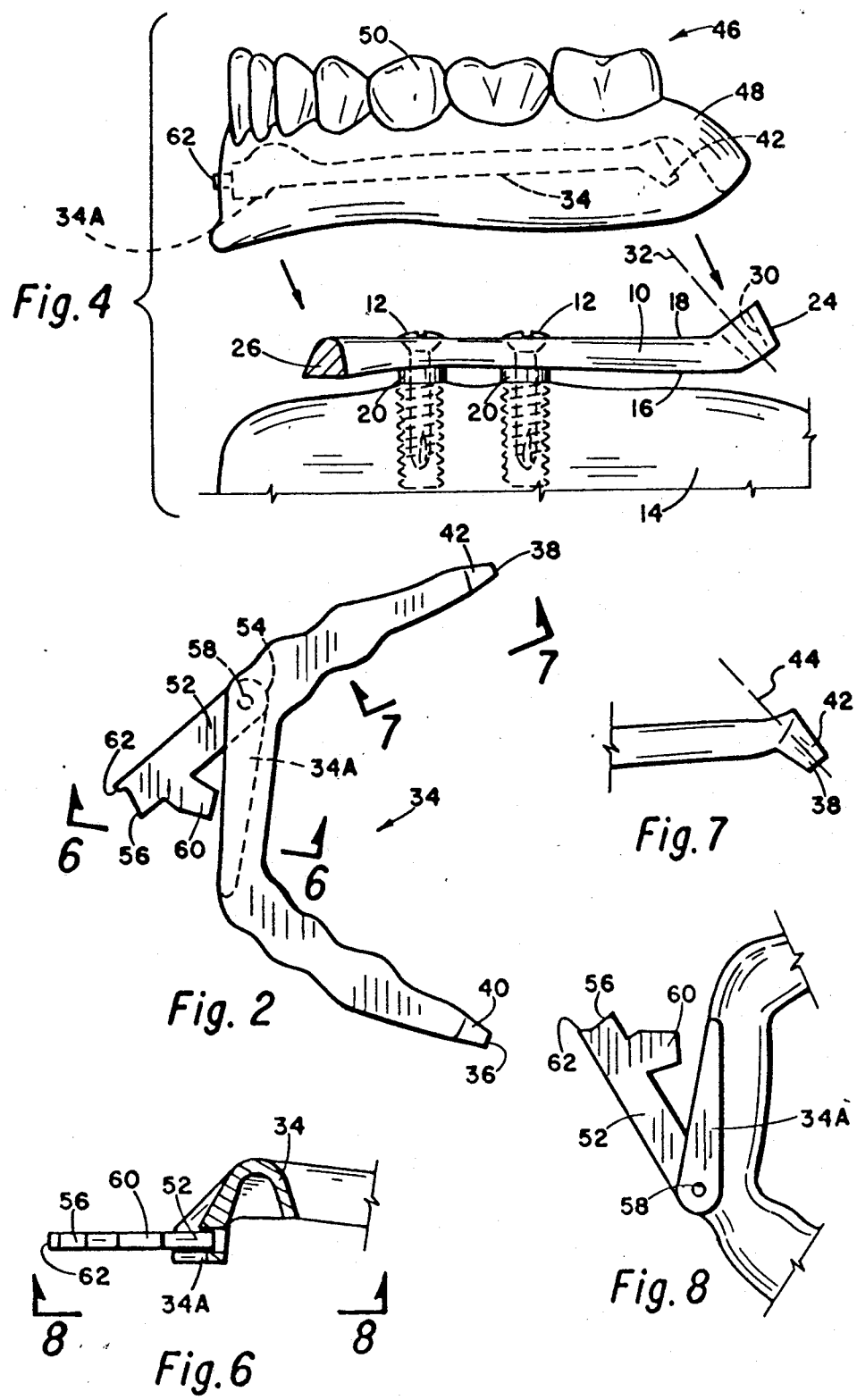

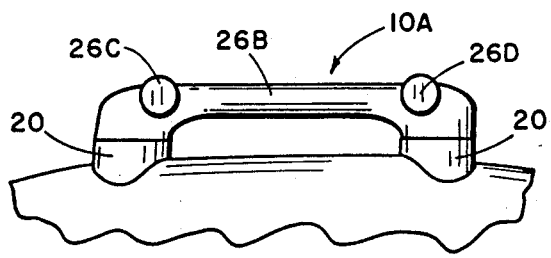
Fig. 11
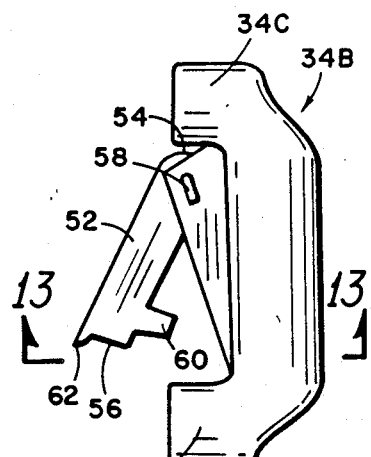
Fig. 12
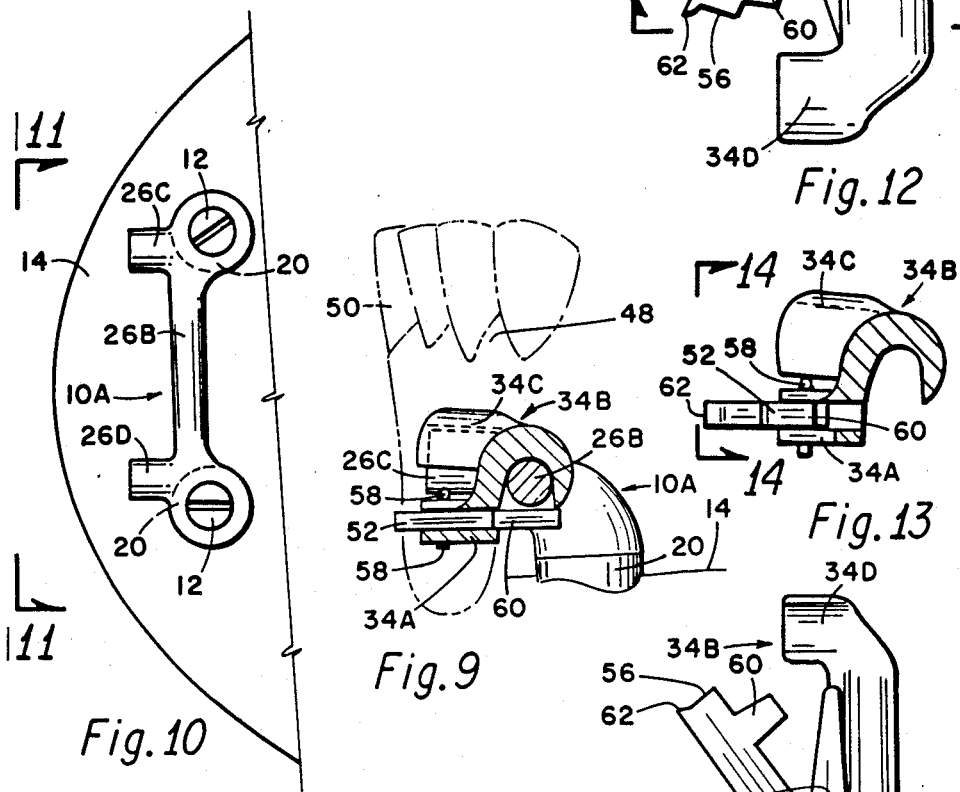
Fig. 9
Fig. 10
Fig. 13
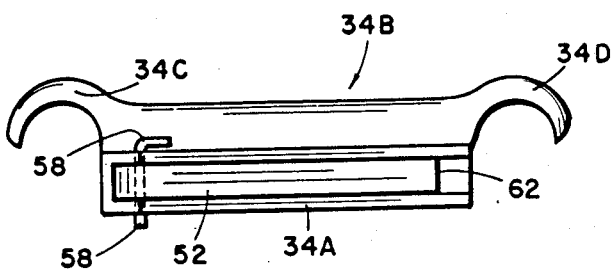
Fig. 14
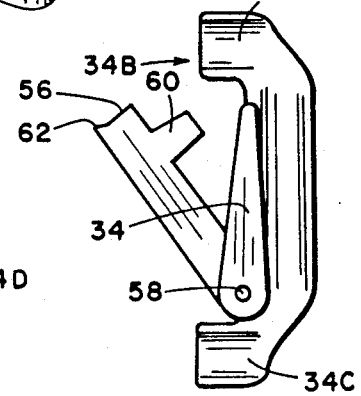
Fig. 15

ATTACHMENT FOR REMOVABLY SUPPORTING A DENTURE IN THE MOUTH OF THE USER

CROSS-REFERENCE

This is a continuation-in-part of application Ser. No. 221,212, filed July 19, 1988, Ralph C. Mays Applicant, entitled "ATTACHMENT FOR REMOVABLY SUPPORTING A DENTURE IN THE MOUTH OF THE USER" which in turn is a continuation-in-part of application Ser. No. 090,456, filed Aug. 28, 1987, Ralph C. Mays Applicant, entitled "ATTACHMENT FOR REMOVABLY SUPPORTING A DENTURE IN THE MOUTH OF THE USER".

SUMMARY OF THE INVENTION

The present invention is directed to an improved means of removably supporting a denture in the mouth of the user. When a person loses all their natural teeth, either upper or lower, but especially lower; the utilization of a denture is and has always been a problem. While dentures can be accurately fitted to the alveolar ridge of the user, it is difficult to retain a denture in position; that is, during normal chewing or talking the denture has a tendency to ride up out of position on the alveolar ridge causing speech difficulties, chewing difficulties, and general unsatisfactory use of a denture.

In recent years a practice has developed of permanently implanting dental posts in the bone structure of the mouth. These permanent metal posts are usually made of titanium which is more readily acceptably by the body's biological processes and which are locked into position by bone growth. By utilization of permanently installed posts in the mouth of the user, the possibility then exists for more readily securing a denture in place.

The present invention provides an improved attachment for removably supporting a denture in the mouth of the user using implants and in which the denture is secured, but in a way so that the denture is very conveniently removed and reinstalled in the user's mouth and wherein decreased stress is placed on the implants.

The attachment is formed by an anchor member which is fitted semi-permanently into the mouth of the user and anchored such as by screws to dental posts. In the usual arrangement the user will have at least two dental posts. The anchor member is preferably a cast member formed by using an impression taken from the mouth of the users after the posts have been installed. In one embodiment the anchor member is generally U-shaped and in a common plane. The U-shaped anchor member has opposed ends and a middle portion. The middle portion is formed by a bar portion which extends between adjacent spaced-apart dental posts and is of generally circular configuration. The anchor member has a proximal surface adjacent to the user's alveolar ridge and an opposed distal surface.

A mating denture member is also cast to substantially conform to the distal surface of the anchor member. The denture member is in this embodiment of U-shaped configuration conforming to the alveolar ridge shape of the user's mouth; and the U-shaped configuration is in a general plane. The anchor member has retention means at the opposed ends. The retention means is in the form of a recess at each end of the anchor member. Each recess is an opening which has an axis which is inclined relative to the plane of the anchor member and in the direction toward the anchor member center portion.

The denture member has retention means in the form of integral projections which are shaped and configured to be removably received within the anchor member recesses. The projections each have an axis of insertion which is at an angle relative to the plane of the U-shaped denture member. The recesses and projections are dimensioned to permit limited movement of the projections within the recesses.

The denture member is utilized by encapsulation in a denture having simulated gums and teeth. The denture member is then integral with the denture member. When the denture is inserted into the mouth of a user, the integral projection extending from the denture member at the ends thereof removably extend into the recesses in the anchor member so that the rear portion of the denture is retained in position but is permitted limited movement.

At or near the central portion of the denture member an arm is pivotally secured at one end. The arm has a blade portion and the arm is pivoted between a locked and an unlocked position. When in the unlocked position the arm extends outwardly, away from the denture member center portion and when in the locked position the arm is moved pivotally toward the center portion so that the blade extends beneath the anchor member bar portion. Thus, when the denture having the denture member cast therein is positioned within the mouth of the user, the integral projections are loosely received in the recesses in the anchor member and the arm is moved to the locked position, the blade of which extends beneath the anchor member bar to thereby lock the denture into the mouth of the user in a manner which permits limited pivotation of the denture about the bar portion.

The outer end of the arm has a fingernail engaging portion. When the user desires to remove the denture, the arm is engaged by the fingernail of the user and is pivoted to the unlocked position allowing the front of the denture to be lifted upwardly and thereby allowing the denture member integral projection to be removed from the anchor member recesses so that the entire denture is easily removed form the mouth of the user.

In an alternate version of the invention two dental posts (as a minimum) are employed in the front of the mouth of the user and with one dental posts being spaced on each side of the center of the mouth. Extending between the dental posts is a bar forming an integral part of the anchor member. The bar has a substantially circular cross-sectional configuration in a plane drawn perpendicular to the length of the bar.

The denture member fits on the anchor member and is removably attached to the bar portion as previously described. A denture having the denture member cast therein is free to pivot about the cylindrical bar. Pivotation in the direction rearwardly of the front of the mouth of the user is desirable for reasons above stated; that is, the alveolar ridge absorbs the pressure of the denture when pivoted in the rearward direction such as when chewing. This takes a substantial amount of the stress off of the post; that is, by permitting pivotation of the denture, twisting action is not applied to the posts so they are less likely to be loosened by action of the dentures.

On the other hand, the pivotation of the denture in the forward direction beyond a small limit is undesirable. For this reason, the anchor member is provided with integral trunnion portions which extend in a plane of the anchor member bar and preferably at substantially right angles to the bar. The denture member has interceptors configured to engage the trunnion members when the denture member is pivoted about the bar a pre-selected number of degrees in the direction towards the front of the mouth of the user. In this manner the denture is prevented from rising forward more than a minimum amount, but is not limited in rearward pivotation. Limiting the forward pivotation is important in the control of a denture, and particularly a lower denture so that excess rising of the denture does not interfere with speech of the user; but at the same time pivotation is allowed in the downward direction so that the alveolar ridge absorbs the force of chewing without causing undue stress on the dental posts.

A better understanding of the invention will be had by reference to the following description and claims taken in conjunction with the attached drawings.

DESCRIPTIONS OF THE DRAWING

FIG. 1 is a top view of an anchor member portion of an attachment for removably supporting a denture in the mouth of the user, the anchor member being shown mounted on posts which have been permanently secured in the bone of the lower jaw of the user. FIG. 1 shows the alveolar ridge of the lower jaw with screws holding the anchor member to the permanently installed dental posts.

FIG. 2 is a top view of the other basic portion of the attachment; that is, a denture member which is cast of metal and configured to be encompassed within a denture. The denture member of FIG. 2 includes an arm pivotable between a locked and an unlocked position, and in FIG. 2 the arm is shown in the unlocked position.

FIG. 3 is an isometric view of a denture which has the denture member of FIG. 2 cast therein and showing the arm extending therefrom in the unlocked position.

FIG. 4 is an exploded view showing the denture of FIG. 1 having the denture member cast therein and showing a portion of the anchor member secured to dental posts permanently mounted into the jaw bone of the user and showing the direction which the denture is inserted onto the anchor member to securely lock the denture to the anchor member within the mouth of the user.

FIG. 5 is a cross-sectional view of a front portion of the mouth of the user showing the alveolar ridge and showing a denture positioned within the mouth of the user and in enlarged dimensions. The anchor member is shown in cross-section and the denture is also shown in cross-section. The denture includes simulated gums and teeth and with the arm in the locked position.

FIG. 6 is a cross-sectional view taken along the line 6—6 of FIG. 2 showing details of the construction of the denture member with the locking arm in the unlocked position.

FIG. 7 is a partial elevational view of an end portion of the denture member showing an integral projection which forms a retention means for retaining the denture in the mouth of the user.

FIG. 8 is a partial lower view of the center portion of the denture member taken along the line 8—8 of FIG. 6 showing the arm in the unlocked position.

FIG. 9 is an elevational cross-sectional view of an alternative embodiment of the invention in which the denture member is pivotal about the anchor member and includes an alternate means of limiting forward pivotation of the denture member.

FIG. 10 is a top plan view of the front portion of the mouth of the user with dental posts therein and with the anchor member of the alternate embodiment of FIG. 9.

FIG. 11 is a front elevational view of the alternate embodiment anchor member attached to two spaced apart dental posts in the mouth of a user.

FIG. 12 is a top plan view of a denture member as shown in FIG. 9 as used with the anchor member of FIGS. 10 and 11.

FIG. 13 is a cross-sectional view of the denture member taken along the line 13—13 of FIG. 12.

FIG. 14 is a front elevational view of the denture member of FIGS. 12 and 13.

FIG. 15 is a bottom view of the denture member as shown in FIGS. 12, 13 and 14.

DESCRIPTION OF THE PREFERRED EMBODIMENT

The attachment of this invention for removably supporting a denture in the mouth of the user is formed of two basic portions. The first portion is an anchor member generally indicated by the numeral 10 and shown in plan view as would be employed for a lower denture in FIG. 1. The anchor member 10 is of the type to be attached to permanently installed dental posts in the user's mouth. Dental posts are inserted into the bone of the user's mouth such as by drilling into the bone and inserting or screwing the posts into position. Other means also are well known for securing posts in the mouth of the user. A dental post typically has a threaded recess therein and FIG. 1 shows the anchor member 10 secured to the dental posts by means of screws 12. The alveolar ridge 14 of the user's jaw is shown.

The anchor member 10 is formed by taking an impression of the mouth of the user after the dental posts are permanently installed. Using this impression the anchor member is cast of metal, and as shown in FIG. 4 has a proximal surface 16 which is adjacent to the top of the patient's alveolar ridge 14 and a distal surface 18 which is opposed to the proximal surface. FIG. 4 shows two of the dental posts 20 with screws 12 therein.

As shown in FIG. 1, the anchor member 10 is of generally U-shaped configuration conforming generally to the shape of the alveolar ridge 14 of the mouth of the user. The U-shaped configuration provides post ends 22 and 24, and a front or middle portion 26 which is intermediate the ends 22 and 24 and between spaced apart dental posts. The front portion forms a bar portion 26 extending across the front or near the front of the anchor member.

At or adjacent the anchor member ends 22 and 24 are retention means which preferably are in the form of recesses 28 and 30. As previously stated, the anchor member 10 is generally of a U-shaped configuration and is in a general plane. Each of the recesses 28 and 30 has an axis, the axis of recess 30 being indicated by the numeral 32 in FIG. 4. The axis of each recess is inclined at an angle relative to the plane of the anchor member. The angle is acute in the direction towards the front of the anchor member or toward the bar portion 26.

The other basic portion of the attachment is a denture member generally indicated by the numeral 34 a top view of which is seen in FIG. 2. The denture member is cast utilizing an impression. The denture member 34 fits in close, substantially contiguous, contact with the distal surface 18 of the anchor member. Like the anchor members, the denture member is generally of U-shaped configuration and in a common plane. The denture member has ends 36 and 38 which are preferably in the form of integral projections 40 and 42. Each of the projections has an axis, the axis of projection 42 being illustrated by the dotted line 44 in FIG. 7. The axis of each projection 40 and 42 is inclined at an acute angle relative to the plane of the denture member 34, and preferably at the same or approximately the same angle as the angle of axis 32 of anchor member 10. The projections 40 and 42 are configured to be slidably inserted into the recesses 28 and 30 of the anchor member and when received in such recesses the denture member 34 cannot be dislodged by a direct upward pull on the denture member, but can only be removed by simultaneous forward and upward movement along the axis 32 of the recess.

The denture member 34 is encapsulated within a denture generally indicated by the numeral 46 in FIG. 3 and 4. The denture included simulated gum portions 48 and teeth 50. When encapsulated in a denture 48 the denture member 34 is exposed on the lower surface thereof to engage the anchor member 10 when the denture is in position. The denture member 34 is preferably of generally U-shaped cross-sectional configuration as shown in FIG. 5 at least in the forward or middle portion thereof with the balance of the denture member generally conforming to the distal surface of the anchor member.

Secured to the denture member 34 in the middle thereof, that is between the opposed ends 36 and 38, is an arm 52 having a first end 54 and second end 56. The first end of the arm 52 is pivoted to the denture member 34 by means of a hinge pin 58. Integrally extending from the arm 52 is a blade portion 60. The second end 56 of the arm has a fingernail receiving portion 62.

To use the denture having the attachment member 34 secured therein in conjunction with an anchor member secured on dental posts within the mouth of the user, the denture is inserted onto the anchor member 10 as shown in FIG. 4; that is, the denture is inserted simultaneously downwardly and rearwardly so that the projections 40 and 42 extend within the recess 28 and 30. The front portion of the denture 46 is then moved downwardly so that the denture member engages the upper surface of anchor member 10. During installation, the arm 52 must be in the open position as shown in FIGS. 2 and 3. When the denture is firmly downwardly in position, the arm is then moved to the closed position shown in FIG. 4 and 5. In the closed position the arm is substantially fully retained within the gum portion 48 of the denture. The fingernail receiving portion 62 of the arm is slightly extended from the surface of the denture gum portion 48 so that when the user wishes to remove the denture his fingernail can be extended underneath the portion 62 enabling him to pivot the arm 52 to the unlocked position.

The denture member 34 includes an integral portion 34A which is below arm 52 and which supports the arm when in the closed position.

The attachment thus provides a highly effective means of anchoring dentures in the user's mouth when the user is having at least two dental posts installed.

Referring to FIGS. 9-15, an alternate embodiment of the invention is illustrated. In this embodiment, only two posts 20 are required although additional posts may be employed. The two indispensable posts are those in the front of and preferably substantially equally spaced to each side of the center of the mouth of the user as shown in FIG. 10. It can be seen that additional posts may be employed for further anchoring the anchor member 10A, however, if such additional posts are employed they will extend rearwardly of the two spaced apart posts 20.

The anchor member 10A is secured to posts 20 by means of screws, as previously described, and includes an integral bar portion 26B extending between the two posts. The bar portion 26B has integrally formed short length trunnions 26C and 26D. The trunnions extend in the plane of the anchor member bar portion 26B and normal to the longitudinal axis of the bar portion.

The denture member 34B is of relatively short length as compared to the denture member describes with reference to FIGS. 1-8, but is utilized in the same way; that is, the denture member 34B as shown in FIGS. 12-15 is received and contained within a denture 48 as shown in FIG. 9. The denture member 34B is integrally configured to conform to the distal surface of the anchor member 10A. The denture member 34B is provided with an arm 52 having a first end 54 and a second end 56 as previously described. The first end of the arm 52 is pivoted to the denture member 34B by means of a hinge pin 58. Integrally extending from the arm 52 is a blade portion 60. The second end 56 of the arm has a fingernail receiving portion 62. In addition, the denture member 34B has integral forwardly extending cusp portions 34C and 34D at the ends thereof. When the denture member 34B is in position with respect to the anchor member 10A, the cusps 34C and 34D extend over and parallel to the anchor member trunnions 26C and 26D. With the denture member 34B encompassed in a denture as shown in FIG. 9, the denture is locked into position by means of arm 52 in the same manner as previously described.

In the embodiment of FIGS. 9 through 15 a different means is provided for limiting the pivotation of the denture relative to the anchor member 10. This pivotation limiting means is achieved by the cooperative action of trunnions 26C and 26D and cusps 34C and 34D. The denture member 34B and anchor member 10A are dimensioned so that when denture 48 having the denture member 34B encompassed therein is in position in the mouth of a user, downward pressure applied to the denture 48 by chewing results in the denture pivoting about the anchor member bar portion 26B. The force of chewing action is applied by the denture member to the rearward portion of the user's alveolar ridge and no torque is thereby applied to the anchor member 10A, and therefore no torque is applied to posts 20. Thus, the trauma of lateral movement of the posts is relieved by the pivotal action of the denture relative to the posts. However, at the same time, the denture is prevented form rising in back; that is, it is prevented from unlimited pivotation in the forward direction around the anchor member bar portion 26B by the engagement of the cusps 34C and 34D with the trunnions 26C and 26D respectively. THus, the combination of the cusps and trunnions limit the pivotation of the denture in one direction, but do not limit the pivotation in the opposite direction in which the alveolar ridge absorbs the force of chewing action by the user.

In application of the embodiment of FIGS. 9-15, the denture will have an appearance as in FIG. 3; that is, the arm 52 is pivoted to the forward direction as illustrated in FIG. 3 to remove the denture, and is pivoted to the closed position to lock it in place as shown in FIG. 9. In the closed position, only a small fingernail engaging portion 62 extends beyond the surface of the denture so as to permit its removal by the user.

The embodiment of FIGS. 9-15 has the same advantages as that described for the embodiment of FIGS. 1-8; that is, the denture mounting arrangement permits pivotation of the denture so that the user's alveolar ridge absorbs the force of chewing, but at the same time upward pivotation of the denture is limited. The main difference between the embodiments of FIGS. 9-15 as compared to that of FIGS. 1-8 is in the method of limiting the upward pivotation of the denture. An additional advantage of the embodiment of FIGS. 9-15 is that the anchor member 10A is of substantially reduced length.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such term used in the prior art and the more specific use of the terms herein, the more specific meaning is meant.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An attachment for removably supporting a denture in the mouth of a user having at least two spaced apart dental posts installed in the user's alveolar ridge, such two posts being in the front of, and one to each side of, the center of the mouth of the user, the attachment comprising:

an anchor member fitable into the mouth of the user for attachment such as by screws to two spaced apart posts in the front of the mouth of the user, the anchor member having a bar portion extending between the two spaced apart posts;

a denture member which conforms generally to the anchor member and is engagable in proximity with said anchor member bar portion, the denture member being castable into a denture having simulated gum portions and teeth portions;

locking means of removably and pivotally interlocking said denture member with said anchor member bar portion when a denture having said denture member formed therein is in usable position with the mouth of the user; and pivotation limiting means formed as a part of said anchor member and said denture member limiting the angle of pivotation in one direction of said denture member to said anchor member about said bar portion when said denture member is interlocked with said anchor member.

2. An attachment member according to claim 1 wherein said anchor member bar portion is elongated and has a longitudinal axis and wherein said bar portion is at least in part substantially circular in a plane taken perpendicular said longitudinal axis.

3. An attachment member according to claim 1 wherein said locking means is in the form of an arm having a first and a second end, and having the first end pivoted to said denture member whereby the arm is pivotal between a locked and an unlocked position, the arm having adjacent the second end a blade portion, and having at the second end fingernail engaging means whereby the second end may be engaged by the fingernail of the user to pivot the arm to the unlocked position, the blade portion engaging said anchor member bar portion when said arm is pivoted to the locked position.

4. An attachment member according to claim 1 wherein said pivotation limiting means includes:

trunnion means extending from said anchor member; and interceptor means extending from said denture member which engage said trunnion means when said denture means has been pivoted a predetermined angle about said anchor member bar portion.

5. An attachment according to claim 1 wherein said pivotation limitation means includes means limiting the pivotation of said denture member about said anchor member bar portion in one direction, but which does not limit pivotation in the opposite direction.

6. An attachment according to claim 5 wherein said pivotation limitation means includes means limiting the pivotation of said denture member in the direction towards the front of the mouth of the user, but which does not limit pivotation in the direction away from the front of the mouth of the user.

* * * * *